(12) United States Patent
Domb et al.

(10) Patent No.: US 8,980,334 B2
(45) Date of Patent: Mar. 17, 2015

(54) DOUBLE-LAYERED ABSORBABLE SOLID COMPOSITIONS FOR THE TOPICAL TREATMENT OF ORAL MUCOSAL DISORDERS

(75) Inventors: Abraham J. Domb, Efrat (IL); Joseph S. Wolnerman, Jerusalem (IL)

(73) Assignee: Axiomedic Ltd., Gilbraltar (GI)

( * ) Notice: Subject to any disclaimer, the term of this patent is extended or adjusted under 35 U.S.C. 154(b) by 159 days.

(21) Appl. No.: 11/611,448

(22) Filed: Dec. 15, 2006

(65) Prior Publication Data

US 2007/0104783 A1    May 10, 2007

Related U.S. Application Data

(63) Continuation-in-part of application No. 10/083,413, filed on Feb. 27, 2002, now Pat. No. 7,943,169.

(60) Provisional application No. 60/271,735, filed on Feb. 28, 2001.

(51) Int. Cl.
| | | |
|---|---|---|
| A01N 65/00 | (2009.01) | |
| A61K 9/00 | (2006.01) | |
| A61K 9/20 | (2006.01) | |
| A61K 31/045 | (2006.01) | |
| A61K 31/56 | (2006.01) | |
| A61K 33/18 | (2006.01) | |
| A61K 36/18 | (2006.01) | |
| A61K 45/06 | (2006.01) | |

(52) U.S. Cl.
CPC .............. *A61K 9/006* (2013.01); *A61K 9/2086* (2013.01); *A61K 31/045* (2013.01); *A61K 31/56* (2013.01); *A61K 33/18* (2013.01); *A61K 36/18* (2013.01); *A61K 45/06* (2013.01)
USPC ........................................................ 424/725

(58) Field of Classification Search
None
See application file for complete search history.

(56) References Cited

U.S. PATENT DOCUMENTS

| | | | |
|---|---|---|---|
| 3,988,433 | A | 10/1976 | Benedict |
| 4,083,955 | A | 4/1978 | Grabenstetter et al. |
| 4,226,848 | A | 10/1980 | Nagai et al. |
| 4,276,287 | A | 6/1981 | Cabardo, Jr. |
| 4,307,075 | A | 12/1981 | Martin |
| 4,615,697 | A | 10/1986 | Robinson |
| 4,772,470 | A | 9/1988 | Inoue et al. |
| 4,915,948 | A | 4/1990 | Gallopo et al. |
| 5,456,745 | A | 10/1995 | Roreger |
| 5,578,315 | A | 11/1996 | Chien |
| 5,719,197 | A | 2/1998 | Kanios et al. |
| 5,939,050 | A | 8/1999 | Iyer et al. |
| 5,942,244 | A | 8/1999 | Friedman et al. |
| 6,063,404 | A | 5/2000 | Timpe |
| 6,159,498 | A | 12/2000 | Topolsky et al. |
| 6,197,305 | B1 | 3/2001 | Friedman et al. |
| 6,207,137 | B1 | 3/2001 | Shuch et al. |
| 6,210,699 | B1 * | 4/2001 | Acharya et al. |
| 6,303,147 | B1 | 10/2001 | Gilis et al. |
| 6,325,991 | B1 | 12/2001 | Draheim |
| 6,458,777 | B1 * | 10/2002 | Sonis et al. |
| 2001/0051186 | A1 * | 12/2001 | Acharya et al. |
| 2007/0048369 | A1 | 3/2007 | Foreman |
| 2007/0104783 | A1 | 5/2007 | Domb |

FOREIGN PATENT DOCUMENTS

| | | |
|---|---|---|
| EP | 0159604 | 10/1985 |
| EP | 0250187 | 12/1987 |
| EP | 0 306 454 | 3/1989 |
| EP | 0 355 536 | 2/1990 |
| EP | 0 449 782 | 10/1991 |
| EP | 0 839 524 | 5/1998 |
| EP | 1236466 | 9/2002 |
| WO | 9500184 | 1/1995 |
| WO | WO 00/18365 | 4/2000 |
| WO | WO 00/59423 | 10/2000 |
| WO | WO 97/24109 | 4/2001 |
| WO | WO 01/70184 | 9/2001 |

OTHER PUBLICATIONS

Barrett, "Homeopathy: the ultimate fake", http://www.quackwatch. com/01QuackeryRelatedTopics/homeo.html (Aug. 9, 1999).

Green, *The Herbal Medicine-Maker's Handbook: A Home Manual*, The Crossing Press, USA, pp. 275-285 (2000).

Guo, "Bioadhesive polymer buccal patches for buprenorphine controlled delivery: formulation, in-vitro adhesion and release properties", *Drug Devel. Ind. Pharmacy*, 20:2809-2821 (1994).

Jianan, et al., "Thermotropic liquid crystalline behaviors of ethylcellulose", *J. Appl Poly. Sci.*, 45:2153-2158 (1992).

(Continued)

*Primary Examiner* — Michael Meller
(74) *Attorney, Agent, or Firm* — Pabst Patent Group LLP

(57) ABSTRACT

Bioadhesive sticker tablets which are applied directly to vaginal, rectal and/or oral mucosa are described herein. In one embodiment, the sticker tablets are applied directly to ulcers or lesions in the oral cavity. The compositions adhere immediately upon administration, swell over time, and remain adherent to the ulcer or lesion for at least 60 minutes. The compositions can be in the form of single layer, double layer, or multilayer sticker tablets. The compositions provide immediate pain relief to the patient and promote rapid healing of the ulcer or lesion. The sticker tablet compositions contain one or more bioadhesive polymers. In one embodiment, the polymers are crosslinked polycarboxylic acids and polyols. The compositions contain at least one herbal agent and/or irritating compound, and optionally, a non-herbal active agent. The compositions can deliver an non-irritating effective dose of the agent for at least 60 minutes. The compositions described herein are stable upon storage for six months or longer.

3 Claims, 1 Drawing Sheet

(56) References Cited

OTHER PUBLICATIONS

Lawless, *The Illustrated Encyclopedia of Essential Oils: The Complete Guide to the Use of Oils in Aromatherapy and Herbalism*, Element Books, USA, pp. 115, 120, 123, 134, 139-141 and 196-197 (1995).

Nagai and Konishi, "Buccal/gingival drug delivery systems", *J. Controll. Rel.* 6(1):353-360 (1987).

Shojaei, "Buccal mucosa as a route for systemic drug delivery: a review", *J. Pharm. Pharm. Sci.*, 1(1):15-30 (1998).

Salamat-Miller, et al. "The use of mucoadhesive polymers in buccal drug delivery", *Adv. Drug Deliv. Rev.* 57(11): 1666-1691 (2005).

Sudhakar, et al. "Buccal bioadhesive drug delivery—A promising option for orally less efficient drugs", *J. Cont. Release* 114(1): 15-40 (2006).

Mizrahi, et al. "Mucoadhesive tablet releasing iodine for treating oral infections", *J. Pharm. Sci.* 96(11):3144-3150 (2007).

Rhee, et al., "Formulation and pharmaceutical properties of mucoadhesive films containing dipotassiumglycyrrhizate", College of Pharm., 29(2)127-136 (1999) Abstract only.

\* cited by examiner

DOUBLE-LAYERED ABSORBABLE SOLID COMPOSITIONS FOR THE TOPICAL TREATMENT OF ORAL MUCOSAL DISORDERS

CROSS-REFERENCE TO RELATED APPLICATION

This application is a continuation-in-part of U.S. Ser. No. 10/083,413 entitled "Absorbable Solid Compositions for Topical Treatment of Oral Mucosal Disorders" by Abraham J. Domb and Joseph S. Wolnerman, filed on Feb. 27, 2002, which claims priority to U.S. Ser. No. 60/271,735 filed on Feb. 28, 2001.

FIELD OF THE INVENTION

This invention is generally in the field of topical compositions for the treatment of oral mucosal disorders.

BACKGROUND OF THE INVENTION

Gingivitis, mucosal lesions, and periodontal disease are common and of unknown etiology. It is generally believed that the primary cause of these disorders is a viral infection or immune response, which leads to bacterial infections or anaerobic bacteria, particularly gram-negative anaerobic bacteria, in the mouth. Periodontal disease is a major cause of tooth loss in adults. Periodontal disease affects the periodontum, which is the investing and supporting tissue surrounding a tooth (i.e., the periodontal ligament, the gingiva, and the alveolar bone). Gingivitis and periodontitis are inflammatory disorders of the gingiva and the deeper periodontal tissues, respectively. Gingivitis results from the buildup of dental plaque, and periodontitis is caused by the infection spreading to the periodontal pocket or space between the gingiva and the tooth root. Microorganisms contribute to both the initiation and progression of gingivitis, plaque, and periodontal disease. Thus, in order to prevent or treat these conditions, these microorganisms must be suppressed by some means other than simple mechanical scrubbing.

Other disorders of the mouth, especially the mucosal surfaces, include herpes labialis (cold sores or fever blisters), herpes genitalis, herpes zoster (shingles), varicella zoster (chickenpox); inflammatory diseases and/or diseases demonstrating compromise and/or reaction of the immune system. These include aphthous stomatitis (canker sores), oral mucositis (stomatitis) secondary to chemotherapy, allergic conjunctivitis, giant papillary conjunctivitis; and lesions of injury to the skin including photodermatitis (sunburn, specifically second degree sunburn), thermal burns and pressure sores (decubitus ulcers).

There are a number of over-the-counter medications for cold sores (fever blisters), canker sores, and oral ulcerations and the like, including BLISTEX®, ZILACTIN®, and CAMPHO-PHENIQUE®. However, for many persons suffering from cold sores, fever blisters, etc., these medications are not very effective. A prescription medication also is available, under the trademark ZOVIRAX®. ZOVIRAX® can be effective when taken orally by interfering with the replication of the herpes virus at the genetic level.

Conventional oral hygiene formulations, such as toothpastes (including gels and gels for subgingival application), mouth rinses, mouth sprays, chewing gums, and lozenges (including breath mints) in general, are not very effective in treating oral lesions due to their short contact time with the lesion surface as well as the environment surrounding the lesion in the oral cavity.

The choice of a carrier to be used is determined by the formulation. U.S. Pat. No. 3,988,433 to Benedict describes carriers suitable for toothpastes. U.S. Pat. No. 4,083,955 to Grabenstetter et al. describes carriers suitable for mouth sprays, lozenges, and chewing gums. The main limitation of these formulations is their short contact time, which is typically only a few seconds. Such short contact times are insufficient for treating lesions associated with the disorders described above.

European Patent No. 0 839 524 to Ronchi describes lozenges composed of common antimicrobial agents such as iodine, benzalkonium chloride, and cetylpyridinium chloride. About 99.5% by weight of the lozenge is highly water soluble sugars like glucose and saccharose in combination with less than 0.5% of a bioadhesive polymer. These lozenges do not stock to mucosal tissue as the amount of adhesive polymer is neglible. The lozenges are candies that have some antibacterial agent which is released as the candies dissolve in the mouth.

U.S. Pat. No. 5,456,745 to Rorger describes certain films that swell in aqueous media. The films are prepared by casting an aqueous solution of water soluble anionic polymers, cationic polymers, and a moisturizer into sheets. The films can be prepared by mixing cationic and anionic polymers without precipitation using co-solvents, volatile additives, heat, etc. The films are suggested for use as dressings for damaged skin, such as ulcers of the leg.

U.S. Pat. No. 5,942,244 to Friedman describes non-adhesive tablets that release herbal extracts. Ethyl cellulose is the main polymer component. Ethyl cellulose is a highly hydrophobic polymer that does not interact with hydrophilic surfaces such as mucosa.

U.S. Pat. No. 5,939,050 to Iyer describes various compositions that contain herbal agents. The compositions are not in tablet form and are not bioadhesive.

U.S. Pat. No. 6,207,137 to Shuch et al. describes an orally absorbable dental formulation. The dental formulation includes a base containing Vitamin C at between about 10% and 25% by weight of the composition, and Co-enzyme Q-10 (or ubiquinone), at between 10 and 25% by weight of the composition.

Bioadhesive films prepared by solvent casting from water soluble components are described in U.S. Pat. No. 4,915,948 to Gallopo et al. The water-soluble bioadhesive material used in this device is a xanthan gum or a pectin combined with a polyol.

U.S. Pat. No. 6,159,498 to Topolsky describes a water-soluble pharmaceutical carrier device composed of a layered flexible film having a first water-soluble adhesive layer to be placed in contact with the mucosal surface, a second, water-soluble non-adhesive backing layer, and a pharmaceutical or combination of pharmaceuticals incorporated in the first or second layer. The first water-soluble adhesive layer is hydroxyethyl cellulose, polyacrylic acid, and sodium carboxymethyl cellulose; and the second water-soluble non-adhesive backing layer is hydroxyethyl cellulose.

Solid medications for placement in the oral cavity described in the prior art have been prepared mainly by solvent casting of solutions containing the actives and the polymers to form films, using heat to evaporate the solvent, that are then cut into devices for placement in the oral cavity. This method of preparation is not suitable for herbal extracts and oils that contain volatile active agents which may evaporate during the manufacturing process. Furthermore, exposure of herbal actives to heat during solvent evaporation may degrade the active agents. In addition, this method is very costly and requires a special production line dedicated for film formation. Further, the use of organic solvents such as ethanol and acetone or chlorinated hydrocarbons to dissolve the polymers is expensive and requires collection of the solvent for disposal in order to protect the environment and may require the use of a fire-proof manufacturing site. Solvent residuals in the films may affect the properties of the films and present a risk of contamination to users. Besides the manufacturing problems and high cost, there is also the problem of film scraps left over from the film cutting process. Finally, mucoadhesive polymer films, prepared by film casting, exhibit poor adhesion to mucosal tissue, related to the manufacturing process.

Systemic delivery of drugs and peptides using the buccal route of administration has also been investigated clinically for the delivery of a substantial number of drugs. Buccal administration is the traditional route of administration for nitroglycerin and is also used for buprenorphine and nifedipine. The buccal mucosa is less permeable than the sublingual mucosa. The rapid absorption and high bioavailabilities seen with sublingual administration of drugs is not observed in the buccal mucosa. The permeability of the oral mucosa is probably related to the physical characteristics of the tissues. The sublingual mucosa is thinner than the buccal mucosa; thus permeability is greater for the sublingual tissue. The palatal mucosa is intermediate in thickness, but is keratinized and thus less permeable, whereas the sublingual and buccal tissues are not keratinized. The use of buccal delivery systems for systemic delivery of drugs has been reviewed by Shojaei, *J. Pharm. Pharmaceut Sci.* 1 (1), 15-30 (1998). A non-degradable device for the delivery of buprenorphine has been described by Guo, *Drug Deliv. Ind. Pharmacy,* 20, 2809-2821 (1994). The buccal delivery of lidocaine and prostaglandins has been reported by Nagai, *J. Controll. Rel.* 6, 353-360 (1987).

While buccal delivery systems have been suggested in the prior art, they have been used primarily for the systemic delivery of drugs by taking advantage of the permeability of the mucosal tissue in the mouth to introduce large doses of drugs, mostly peptides and proteins, into the blood system by a non-invasive method. Buccal delivery allows the drug to bypass the gastrointestinal tract, which can degrade drugs which are acid labile and is much less permeable to this class of drugs. Due to the safety risk of systemic uptake of drugs delivered by buccal delivery, the use of natural and safe herbal medications provide an attractive alternative for treating oral ulcers with high patient compliance.

There exists a need for an effective and convenient remedy for the symptoms of viral diseases such as herpes labialis (cold sores or fever blisters), herpes genitalis, herpes zoster (shingles), varicella zoster (chickenpox); inflammatory diseases or diseases comprising the immune system such as aphthous stomatitis (canker sores), oral mucositis (stomatitis) secondary to chemotherapy, allergic conjunctivitis, giant papillary conjunctivitis; and lesions of injury, thermal burns and pressure sores.

It is therefore an object of the invention to provide an improved convenient non-irritating and safe medication and treatment for viral diseases and disorders.

BRIEF SUMMARY OF THE INVENTION

Bioadhesive sticker tablets which are applied directly to vaginal, rectal and/or oral mucosa are described herein. In one embodiment, the sticker tablets are applied directly to ulcers or lesions in the oral cavity. The compositions adhere immediately upon administration, swell over time, and remain adherent to the ulcer or lesion for at least 60 minutes. The compositions can be in the form of single layer, double layer, or multilayer sticker tablets, which are prepared using conventional compression tableting methods. The compositions provide immediate pain relief to the patient and promote rapid healing of the ulcer or lesion. The sticker tablet compositions contain one or more bioadhesive polymers. In one embodiment, the polymers are crosslinked polycarboxylic acids and polyols. The compositions contain at least one herbal agent and/or irritating compound, and optionally, a non-herbal active agent. The compositions can deliver a non-irritating effective dose of the agent for at least 60 minutes. The agent is typically in the form of an extract or oil. In another embodiment, iodine is complexed to ethyl cellulose or hydroxypropyl cellulose, and the complex is incorporated into a mucoadhesive polymeric sticker tablet. The iodine sticker tablets exhibit antifungal and antibacterial properties. The compositions described herein are stable upon storage (i.e. retain an effective amount of the herbal agent or agents) for six months or longer.

DETAILED DESCRIPTION OF THE INVENTION

I. Definitions

Figure 1:
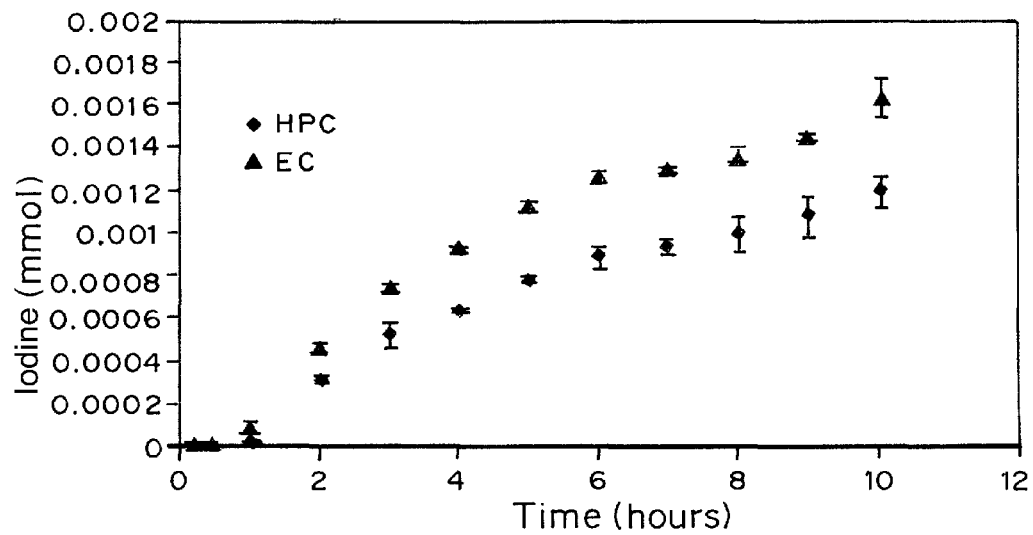
FIG. 1 shows the release profile of iodine (mmol) versus time (hours) in a pH 7.4 phosphate buffer from bioadhesive double-layer sticker tablets prepared from hydroxypropyl cellulose (HPC) and ethyl cellulose (EC).

"Adhesive", as used herein, refers to any substance, organic or inorganic, natural or synthetic, that is capable of surface attachment to the intended oral cavity application site.

"Bioadhesive", as used herein, refers to a material which attaches, and preferably strongly attaches, to mucosal tissue upon hydration. The material must be capable of remaining adhered to the tissue in moist or wet in vivo environments. The compositions described herein are "self-bioadhesive" in that they attach to the site of interest without the need to reinforce attachment by way of another adhesive which is applied as a backing.

"Herbal agents" and "herbal active agents" are used interchangibly herein and refer to a plant or plant part used for its therapeutic properties. The herbal agents described herein are effective in treating various oral mucosal disorders. The herbal agent may be a plant extract, tea, oil (e.g. essential oil), tincture, etc. "Essential oil" and "volatile oil" are used interchangeably herein and refer to a liquid with a high vapor pressure or low boiling point, usually having the characteristic odor or flavor of the plant from which it is obtained. Volatile oils evaporate at standard temperatures and pressures.

"Irritating compound", as used herein, refers to an agent that induces a state of irritation when applied directly to mucosa. The state of irritation may be in the form of inflammation, swelling, redness, or a painful reaction to the agent.

"Volatile compound", as used herein, refers to compounds or materials that sublime, evaporate, or partially evaporate at temperature from about 20° C. to 40° C. at atmospheric pressure. The degree of evaporation is at least 1% of the weight of the compound or material within one hour under the described conditions. Examples of voltatile compounds include, but are not limited to, volatile oils.

"Plant extract", as used herein, refers to compounds and materials obtained from plants.

"Tincture", as used herein, refers to a plant extract prepared by steeping or soaking one or more plant materials in an alcohol or alcohol-water solvent.

A "non-irritating effective dose", as used herein, refers to a dose that does not cause adverse effects to a degree that a patient could no longer tolerate the composition. This is measured by the degree of redness, swelling, and/or patient discomfort.

II. Compositions

The compositions described herein contain an active agent and a pharmaceutically acceptable solid bioadhesive carrier. Typically the active agent includes at least one herbal agent, volatile compound or irritating compound, or a combination thereof. The compositions are in the form of a sticker tablet. Following application to a mucosal surface, the compositions typically adhere to the surface for at least 30 minutes.

The compositions adhere immediately upon administration, swell over time, and remain adherent to the ulcer or lesion for at least 60 minutes.

The compositions can be in form of a single layer, double layer, or multilayer sticker tablet, which are prepared using conventional compression tableting methods. The compositions provide immediate pain relief to the patient and promote rapid healing of the ulcer or lesion. In one embodiment, the composition is a flexible, bioadhesive tablet.

Dual layer sticker tablets containing a bioadhesive side from which the agent is released and an inert backing layer are prepared by applying an inert, hydrophobic, non-adhesive coating to one side of the tablet. In one preferred embodiment, the bioadhesive dual layer tablet comprises a therapeutically effective amount of at least one irritating volatile active agent for treating an oral disorder; a delivery layer suitable for delivery of a non-irritating effective doses of the agent for at least 60 minutes and a bioadhesive layer composition in a defined predetermined size that adheres to the buccal or mucosal surface and stays at the site for at least 30 minutes, preferably for at least 60 minutes. The carrier composition may contain an acceptable plasticizer for the bioadhesive material, and a cohesive agent.

A. Bioadhesive Materials

Suitable adhesive materials include, but are not limited to, carboxylic acid containing polymers such as copolymers of acrylic or methacrylic acid; esterified polyacrylic acid polymers, such as polyacrylic acid polymers lightly crosslinked with a polyalkenyl polyethers (commercially available from B.F. Goodrich, Cincinnati, Ohio, under the trademarks CARBOPOL® 934, 934P, 974, 940 and 941); maleic acid copolymers; polysaccharides such as karaya gum, tragacanth gum, xanthan gum, jaraya gum, pectin, guar gum, locust bean gum, psyllium seed gum, alginates, hydrocolloid gels prepared from polysaccharides extracted from *Fronia elephantum, Sapindus trifoliatus, Kunjac*, and the cashew tree; cellulose and cellulose and cellulose derivatives such as carboxy methyl cellulose, hydroxy propyl cellulose, mixtures thereof, and mixtures of sulfated sucrose and aluminum hydroxide, along with other substances known for use in transdermal preparations capable of forming a solid colloid that can adhere to tissue, used alone or in combination with other suitable carriers. In one embodiment, the bioadhesive material is a mixture of crosslinked polyacrylic acid, i.e. CARBOPOL® 940, 934, 974, carboxymethyl cellulose (CMC) and hydroxypropylmethyl cellulose (HPMC). The strength of adherence can be measured by standard tests for measuring the force, e.g. in dynes per square centimeter, as disclosed in U.S. Pat. No. 4,615,697 to Robinson.

B. Active Agents

The compositions contain at least one herbal agent, volatile agent, and/or irritating compound. Optionally, the compositions contain, in addition to one or more herbal agents, volatile, and/or irritating compounds, a non-herbal active agent. The herbal, volatile, and/or irritating compounds may have anti-inflammatory, analgesic, antiaching, anesthetic, antimicrobial, antifungal, antiseptic, antiviral, antibiotic, or antiparasitic activity, or combinations thereof.

Herbal Agents

Suitable herbal agents include, but are not limited to, essential oils, plant extracts (including volatile and non-volatile extracts), tinctures, and herbal medications composed of one or more herbal extracts that have anesthetic, antiviral, anti-inflammatory, antiproliferative, antibacterial and/or antifungal activity.

In one embodiment, the active agent is an essential oil and/or plant extract that is volatile and an irritant when placed directly on the mucosal tissue. Suitable essential oils and/or plant extracts include, but are not limited to, citronella oil, lemon oil, citron oil, cedarwood oil, juniper berries oil, lemon basil oil, *rosimarinus offencinalis* oil, cinnamon oil, cajeput oil, eucalyptus oil, fennel oil, geranium oil, girofle oil, lavender oil, clove oil, spearmint oil, myrte oil, orgigano oil, pine oil, rosemary oil, sarriette oil, thyme oil, and tea-tree oil. In one embodiment, the essential oil is cinnamon oil, tea-tree oil, citronella oil, or a combination thereof.

Suitable plant extracts include, but are not limited to, *Taraxacum platycarpum H. Dahlstedt, Gardenia jasminoides Ellis, Lonicera japonica Thunberg, Scutellaria baicalensis Georgi, Pulsatilla koreana Nakai, Pueraria thumbergiana Bentham*, and combinations thereof.

The essential oil and/or plant extract is present in a concentration from about 0.02% to about 90% by weight of the composition, more preferably from about 5% to about 50% by the weight of the composition.

In another embodiment, the active agent is a tincture. Suitable tinctures include, but are not limited to, tinctures of Plantago, Hypericum, Echinacea, Baptisia, Calendula, Myrrah, Phytolaca, Salvia, Catechu black, Coneflower, Krameria, Tsuga, grape fruit seed extract, Rosmarinus, Styrax, Crataegus, Glycerrhiza, Angelica, Krameria, Matricaria, Mallow, Propolis and Sage, Barberine from Hydrastis Canadensis L. and other Berberidaccae plant families. Gentian from the Gentianaceae family of plants, monoterpenes of three unsaturations, and combinations thereof. The term "monoterpenes of three unsaturations" as used herein, refers to a composition containing at least one monoterpene of three unsaturations of the molecular formula $C_{10}H_{16}$, wherein the sites of unsaturation are double bonds and/or a cyclization. Examples of monoterpenes with three unsaturation include, but are not limited to, limonene, which contains two double bonds and one cyclic group; myrcene, which contains three double bonds; sabinene, a-pinene and b-pinene.

Irritating Compounds

Suitable irritating agents include, but are not limited to, menthol, salicylic acid, benzoic acid, aspirin and an aspirin like agents, oxidizing agents such as hydrogen peroxide, permanganate and benzoyl peroxide, malachite green, short chain alcohols, concentrated NaCl and iodine. Concentrated plant extracts and oils are usually irritating to the oral mucosa and need to be diluted to reduce irritation. Examples of such oils and extracts include, but are not limited to, lemon oil, geranium oil, peppermint oil, turpentine oil. Mucosal irritating compounds that cause stomach or skin irritation at certain concentrations are suspected to cause oral mucosal irritation depending on the concentration and/or contact times. In one embodiment, the irritating active agent is iodine. The concentration of iodine is typically from about 0.01 to about 10% by weight of the composition, preferably from about 0.1 to about 5% by weight of the composition. In another embodiment, the irritating agent is menthol. The concentration of menthol is typically from about 0.1 mg to about 20 mg, preferably from about 0.5 mg to about 3.0 mg per one centimeter tablet. The degree of irritation and/or the effect on the mucosal tissue is dependent on the amount of the irritant that is in contact with the mucosal tissue and the amount of time the irritant is in contact with the mucosal tissue. The degree of irritation and/or the effect on the mucosal tissue varies for different irritants. Very irritating agents may cause burning of the tissue with subsequent loss of the tissue layers that are in direct contact with the irritant. Irritants may cause localized pain, redness, and/or swelling that can last for hours, even days, after the agent has been removed from the mucosal tissue. Less irritating agents typically cause redness and/or minor swelling that lasts for only a few hours.

Non-herbal Active Agents

The compositions optionally contain one or more non-herbal active agents, such as local anesthetics, analgesics, antivirals, antimicrobials, steroidal and non-steriodal anti-inflammatory agents, antihistamines or antiallergics, steroids, enzymes, vitamins, antipyretics, anti-malarial agents, and anti-ulcer drugs, peptides, DNA plasmid and antisense based therapeutic agents, anti-proliferatives, antifungal agents, and combinations thereof.

Suitable local anesthetics include, but are not limited to, benzocaine, lidocaine, dibucaine, and etidocaine. Suitable synthetic antifungal agents include, but are not limited to, azole compounds such as fluconazole, timidazole, secnidazole, miconazole nitrate, econazole, haloprogin, metronidazole, itraconazole, terconazole, posaconazole, ravuconazole, ketoconazole, clotimazole, and sapirconazole, C. Carrier, Additives, and Excipients Formulations are prepared using a pharmaceutically acceptable "carrier" composed of materials that are considered safe and effective and may be administered to an individual without causing undesirable biological side effects or unwanted interactions. The "carrier" includes all components present in the pharmaceutical formulation other than the active ingredient or ingredients. The term "carrier" includes, but is not limited, to diluents, binders, stabilizers, flavoring agents, sweetening agents, pigments, humectants, lubricants, disintegrators, and fillers.

Suitable humectants include, but are not limited to, edible polyhydric alcohols, such as glycerin, sorbitol, xylitol, butylene glycol, polyethylene glycol, and propylene glycol. In one embodiment, the humectant is sorbitol and/or glycerin. The humectant may also act as a plasticizer to provide a flexible sticker, which is comfortable to the user when placed in his/her mouth. The concentration of the humectant is from about 1% to about 20% by weight of the composition, preferably from about 1% to about % by weight of the composition.

Suitable flavoring agents include, but are limited to, oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and combinations thereof. The concentration of the flavoring agent is from about 0.001% to about 1% by weight of the composition. Some of the compounds listed as excipients and carriers can also be active agents depending on the concentration of the compound in the composition. For example, menthol at a concentration of 0.01% by weight is typically a flavoring agent but at a concentration of 2.0% by weight can be an active agent.

Sweetening agents include, but are not limited to, sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and combinations thereof. The concentration of the sweetening agent is from about 0.1% to about 2% by weigh of the composition, preferably from 0.1% to about 1% by weight of the composition.

D. Cooling and Salivating Agents

Cooling agents, salivating agents, warming agents, and numbing agents can also be included in the compositions. The concentration of these agents is from about 0.001% to about 10% by weight of the composition, preferably from about 0.1% to about 1% by weight of the composition. Suitable cooling agents include, but are not limited to, carboxamides, menthol, ketals, diols, and combinations thereof. Suitable salivating agents include, but are not limited to, Jambus™ manufactured by Takasago. Suitable warming agents include, but are not limited to, capsicum and nicotinate esters, such as benzyl nicotinate. Suitable numbing agents include, but are not limited to, benzocaine, lidocaine, clove bud oil, and ethanol.

E. Hydrophobic Coating Materials

Dual layer sticker tablets containing a bioadhesive side from which the agent is released and an inert backing layer can be prepared by applying an inert, hydrophobic, non-adhesive coating to one side of the tablet. Typical hydrophobic powders suitable for this coating include: fatty acids and salts such as Mg- or Ca-stearate, triglycerides and fatty acid esters, ethyl cellulose, methyl methacrylate-methacrylic acid copolymers (EUDRAGIT®), and other pharmaceutically acceptable hydrophobic components. To improve the adherence between the coating and the tablet, the hydrophobic components are mixed with the carrier components, such as for example, HPMC and CARBOPOL® at a ratio of 30 to 70% by weight.

The inert backing layer typically also serves as a delivery layer. In one preferred embodiment, the delivery layer is suitable for delivery of a non-irritating effective doses of the agent for at least 60 minutes. Typically the delivery layer contains a polymer or polymer mixture that slowly erodes when placed in aqueous media and the active agent dispersed as is or encapsulated or complexed with a carrier. The amount of polymer carrier is enough to control the delivery of safe amounts of the active agent toward the treated mucosal tissue. For example, polyvinyl pyrrolidone powder having a molecular weight of 90,000 is mixed with dextrose and EUDRAGIT® E at a weight ratio of 4:1:1 is mixed with a fine powder of menthol to form a powder containing 2% by weight menthol. This powder can be compression molded to form bilayer tablets. The typical amount of powder per tablet is in the range of 50 to 100 mg. The ingredients and ratios are dependent on the desired erosion rate, flexibility of the tablet, swelling rate and degree, and the release profile of the active agent. These parameters can be adjusted based on the specifications when higher molecular weight polymers and more hydrophobic polymers, which have longer erosion times, are used. Hydrophilic additives such as polyethylene glycol, sugars, and salts can be incorporated to increase the erosion rate and thus the release rate of the active agent.

III. Method of Making the Compositions

A. Preparation of Dried Herbal Extracts/Essential Oils

Because of the limited size of the sticker tablet and the loading, the active agent should be as concentrated as possible. In addition, because the sticker tablet is prepared by molding of a powder mixture in a tableting machine, a free flowing powder suitable for use with commercial tableting devices is preferably used to form the sticker tablet.

Typically, hydroalcoholic herb extracts, upon solvent evaporation, form a sticky mass that can not be incorporated homogeneously with an inert excipient to form free flowing powders. To overcome this limitation, methods have been developed in which the herbal extracts are absorbed into or onto an inert free flowing powder at high concentrations, which are then mixed with the bioadhesive ingredients to form a free flowing powder prior to press molding. In one embodiment, a water soluble pharmaceutically acceptable component, such as a sugar, is added to the herbal extract solution, which is freeze dried to form a dry, free flowing powder. The amount of loading is expressed in terms of the amount equivalent to the dry weight, in grams, of the extracted plant per gram of inert absorbent material (sugar). For example, if 2 g of mannitol is dissolved in a given tincture of 100 ml prepared from the extraction of 10 g of a plant, and the solution is lyophilized to dryness to form a powder, which weighs 2.5 grams, then each gram of this powder is equivalent to 4 grams of plant extract.

When essential oils are incorporated into the sticker tablet, the oil is absorbed onto a suitable absorbent material in powder form. Typical absorbents include, but are not limited to, kaoline, Kapectin™, alumina, silica, polystyrene beads, polyacrylate beads, clay, microcrystalline cellulose, and other orally acceptable powders with oil absorption capacity. Essential oils can also be absorbed onto a crude herbal extract, in powder form, that is part of the active agent.

A typical process of preparing the crude herbal material for extraction is as follows:

1. The crude dry herbal materials are milled into fine powders using a milling device. Any grinding operation that achieves the respective particle size for extraction is acceptable. Suitable particle sizes are in the range of 100 microns to 1,000 microns. Milling is necessary to ensure that crude, dried plant material is consistently-sized. Crude herb extractability is dependent on the ratio of the exposed surface area of crude herb powder to the mass of the hydroalcohol solvent. Other extraction solvents that can be used include, but are not limited to, ethanol, propanol, hot or cold water, diethyl ether, tetrahydrofuran ethyl acetate, and combinations thereof. To eliminate crude herb particle size as a process variable and since the various herbs have different water-holding capabilities (porosity/absorptivity), a singular particle size is preferred for process control. Depending on the specific type of crude herbs, milling produces a mix of coarse and fine dust particulates.

2. All milled crude herb powders are mixed in a blender to provide a uniform particle size of the crude herbal powder prior to extraction. The particle size of the milled crude herbal powder is consistent following this step.

3. The crude herbal powder can be extracted with hydroalcohol solutions using a variety of methods. Two suitable methods for preparing the compositions described herein are described below.

a) Soxhlet method: approximately 1-60 parts of milled crude herbal powder are added to 100-5000 parts (process and/or deionized or equivalent grade) water:alcohol in a Soxhlet Extractor and then decanted. The powder is generally extracted for a period of up to 48 hours.

b) Ultrasonics method: a suitable alternate extraction process for preparing the water soluble extract includes the use of ultrasonic water extraction systems which can provide equivalent quality, depending on the herb, with up to 94% faster process cycles. Suitable ultrasonic water extraction systems includes hydrolysis extracting reactors, fixed bed extracting reactors, desorption extraction columns, and countercurrent extractors.

4. The water-extracted herbal liquid is filtered (e.g., 5-100 micron filter cartridge, fine screen or cheesecloth) or centrifuged to remove coarse and/or insoluble particulates.

5. The filtered water-extracted herbal liquid is concentrated, depending on herbal ingredient, up to a 50% soluble solids level. In addition to concentration by evaporation, alternate suitable processes to achieve higher concentrations prior to final drying include freeze concentration, partial freeze drying, membrane separation, vacuum distillation and vacuum drying.

6. The concentrated herbal extract liquids are dried via commercial drying processes. Suitable dryers that can be used include fluidized bed, vacuum plate, spray, drum-type and flash dryers. Drying efficiency is controlled for water content (<10%) and free water considerations (≤0.80) to achieve shelf-stability. The yield of soluble powder from the drying process is used as a key to optimize the herb:water mass ratio for extraction.

7. The dried pure solid herbal extract powders are sized and packaged for shipment. Desiccating materials such as a silica gel or other suitable FDA-approved, drying agents can be used to control relative humidity and to improve shelf-life.

8. The dried pure solid herbal extract powder is now ready for reconstitution into oral care products.

B. Preparation of Bioadhesive Sticker Tablets

Compression Molding

Compression molding can be used to prepare single layer, dual layer, or multilayer sticker tablets. The simplest method for preparing the sticker tablets is by compression molding using a single or multi-punch press machine. The powder is loaded in the punch having a diameter ranging from about 4 to about 15 mm and a thickness of about 0.5 mm to about 2.5 mm. The thickness is defined by the amount of powder added, usually between about 50 mg and 250 mg. The powder is compressed to form a single layer sticker tablet.

Dual layer sticker tablets are prepared using the double compression technique. The inert powder is first added to the punch to cover the surface. The formulation powder is added on top and compression is applied to produce a sticker tablet where one side is bioadhesive and the other is not. The non-bioadhesive side also tends to be less water-permeable than the bioadhesive side. Alternatively, one powder is added to the punch and compressed to form a thin tablet. The second powder is then added and compressed to form a uniform bilayer tablet.

Spray Coating

Dual layered sticker tablets can also be prepared by spray coating. In the spray coating method, the coating is applied by spraying an alcoholic solution or fine dispersion of a hydrophobic coating material onto one side of the sticker tablet. The spray coating can be applied using an automated machine where the tablets are placed onto a running sheet which is exposed to spray nozzles to spray coat the tablets. Typical hydrophobic powders suitable for this coating include: fatty acids and salts such as Mg- or Ca-stearate, triglycerides and fatty acid esters, ethyl cellulose, methyl methacrylate-methacrylic acid copolymers (EUDRAGIT®), and other pharmaceutically acceptable hydrophobic components.

Solvent Casting

Another way of preparing thin single layer sticker tablets is by casting a concentrated suspension in ethanol of all tablet ingredients onto a flat surface where, after solvent evaporation, a thin sheet is obtained. The sheet is then cut into films of the desired size and shape using a cutting mold.

Dual layered films can be prepared by applying the coating as a spray on top of the sheet loaded with the active agents. Other industrial methods can be used, such as forming the sheet on an edible hydrophobic sheet such as rice paper and cutting the sheets into the desired size.

C. Dosages

The compositions described herein are administered in appropriate sizes to avoid discomfort in the patient's mouth. In one embodiment, the surface area of the tablet is from about 0.4 cm$^2$ to about 3 cm$^2$, preferably from about 0.5 cm$^2$ to 1.8 cm$^2$, more preferably from 0.5 cm$^2$ to 1.2 cm$^2$. For example, a tablet having a diameter of 15 mm, will have a surface area of approximately 1.8 cm$^2$.

The active agent is loaded into the composition in as high a concentration as necessary to produce the desired therapeutic result with minimal side effects on mucosal tissue. The desired loading of active agent in the tablet is dependent on the disorder to be treated, the agent to be delivered, and the desired therapeutic effect. In general, the loading of active agent ranges from about 0.1 mg/cm$^2$ to about 50 or more mg/cm$^2$ depending on the effectiveness and safety of the active agent and the total dose of active agent applied. For example, 2 mg of menthol per 100 mg tablet, which is applied to the treatment site for two hours is sufficient.

IV. Methods of Administering the Compositions

The sticker tablet is applied to the oral mucosa to treat diseases or conditions of the oral cavity. Alternatively, the sticker tablet can be applied to another mucosal surface, such as the vaginal or rectal mucosa. The bioadhesive sticker tablet adheres to the mucosa for at least 30 minutes, preferably from about 1 hour to about 24 hours, more preferably from about 3 hours to about 10 hours. The method often involves expectoration of most of the composition following the desired period of contact.

The sticker tablet is preferably administered from about once a day to four times per day, more preferably from about once per day to about twice per day. The period of such treatment typically ranges from about one day to about 7 days. For particular oral care diseases or conditions, the duration of treatment depends on the severity of the oral disease or condition being treated, the particular delivery form utilized, and the patient's response to treatment.

EXAMPLES

Materials

Hydroxypropyl cellulose (HPC) with a weight average molecular weight of 1,150,000 Da, a viscosity of 1500-3000 mPa/s (1% aqua's solution), and an ethoxy content of over 45% was obtained from Hercules Co., Ltd. (KLUCEL® HF, Wilmington, Del.). Ethyl Cellulose (EC), having a viscosity 6-8 cP (5% solution in 80% toluene and 20% ethanol) and an ethoxy content of 48-49.5% was obtained from Dow Chemical, Midland, Mich. (sold as ETHOCEL® Premium). CARBOPOL® 934 (CP) was obtained from Goodrich Co., Ltd. (Cleveland, Ohio). Potassium iodide was obtained from J. T. Baker (Phillipsburg, N.J.) and Iodine from Merck & Co., Inc. NJ.

Instrumentation

UV-Visible spectra of iodine-doped membranes were recorded using a UV-VIS scanning spectrophotometer (Ultrospec 2100 Pro; Biochrom. Cambridge, UK). Thermal analysis was determined on a Metler TA 4000-DSC differential scanning calorimeter, calibrated with Zn and In standards, at a heating rate of 10° C./min in an atmosphere of nitrogen. The average sample weight was 5-15 mg.

Example 1

Preparation of Herbal Extract Powders

Herbal medicine extracts were obtained by adding 30 g each of *Taraxacum platycarpum H. Dahlstedt, Gardenia jasminoides Ellis, Lonicera japonica Thunberg, Scutellaria baicalensis Georgi, Pulsatilla koreana Nakai* and *Pueraria thumbergiana Bentham*, which were cut and dried, to a cosolvent containing 300 ml of water and 300 ml of ethanol. The mixtures were shaken or refluxed for 3 hours to extract the medicinally useful substances. After extraction, the extracts were poured through a filtering paper. The filtered extracts were centrifuged and decanted. Sugar powder (mannitol or dextrose) was added (1 gram of sugar per 10 gram equivalent of dried plant), and the solution was freeze dried to obtain a fine flowing powder. The amounts of the obtained herbal extracts on the basis of dry solid substances were: 6.2 grams, 9.4 grams, 7.7 grams, 7.7 grams, 9.2 grams, and 9.5 grams, respectively. Other plant extract powders were prepared similarly by adding to the extract solution an inert component such as a sugar, microcrystalline cellulose, titanium dioxide, silicone dioxide, talc, or other inert powders. All calculations for the active agent were based on the weight of the dried plants.

Preparation of Dried Powders of Essential Oils

Essential oils, such as limonene, and other oils to be incorporated in a sticker tablet, were absorbed into absorbing powders such as talc, microcrystalline cellulose, titanium dioxide, silicone dioxide, polystyrene beads, methacrylates, or other pharmaceutically acceptable solid powders with absorption capacity. Typically, 1 g of the following oils: limonene, pinenes, myrcene, terpinene, citron oil, orange oil, mint oil, clove oil, lemone oil, and pumela oil, were each mixed with 2 grams of talc, hydroxypropyl methyl cellulose (HPMC), or silicone dioxide. After about one hour, a free flowing powder was obtained.

Example 2

Preparation of Bioadhesive Sticker Tablets 15 mg of a white powder composed of 50% MG-stearate, 33% Carbopol 934, and 17% HPMC, was added to a laboratory punch and slightly rotated to obtain uniform coverage over the surface of the punch. To this was added a mixture composed of 7 mg of plant extract and 63 mg of a powder mixture of Carbopol™ 934 and hydroxypropyl methylcellulose (HPMC) (2:1 weight ratio). The powder was compressed into a sticker tablet at a pressure of 7 tons per cm$^2$ for 30 seconds. Uniform strong dark sticker tablets with a white coating on one side were obtained. To evaluate how the ratio of Carbopol™ 934 and hydroxypropyl methylcellulose (HPMC) affect the bioadhesive properties of the tablets, formulations containing from 2:1 w/w to 10:1 w/w Carbopol™ 934 to hydroxypropyl methylcellulose (HPMC) were prepared. The formulation containing 4:1 Carbopol™ 934 to hydroxypropyl methylcellulose (HPMC) provided adhesion for 6-8 hours.

A multi layer sticker tablet was prepared by compression of three different powders, the first layer being a thin layer of self adhesive powder, Carbopol™ 934:HPMC (2:1 w/w ratio) loaded with benzocaine, a local anesthetic. The second layer was loaded with the herbal active agents and the third layer was a capping layer of a hydrophobic water-soluble material, such as magnesium stearate and Carbopol™ 934 and HPMC. The main advantage of using a multilayer sticker tablet is that each layer may contain different active agents that are released at different times and rates to the mucosal surface for more effective treatment.

Example 3

Preparation of Herbal Sticker Tablets with Antimicrobial and Anti-Inflammatory Activity Sticker tablets were prepared by compression molding of an herbal active composition in powder form and mixtures of Carbopol 940 and HPMC and other inert ingredients. Table 1 below lists the herbal active agents and their activity.

TABLE 1

Herbal Active Agents and their Medicinal Activity

| Herbal Active Agent | Activity |
| --- | --- |
| *Calendula* | Anti-inflammatory |
| Blood root | Antibiotic, anti-inflammatory |
| Goldenseal | Antiseptic, antibiotic |
| *Aloe vera* | Analgesic, anti-inflammatory |

The herbal extracts, with a concentration of 1 ml extract equivalent to 1 gram of dried plant material, were mixed together at equal volumes. Mannitol was added in a concentration of 1 g of mannitol per 10 g of dried plant material to provide a powdery material. The material was lyophilized to dryness. A dark dry powder was obtained which was used to prepare compressed sticker tablets.

The materials listed in Tables A, B, C, D, and E were compressed into 80 mg sticker tablets, which were then coated on one side with a cap coating. Each table is followed by a description of the materials used in the cap coating.

TABLE A

| Ingredient | Amount (mg) |
| --- | --- |
| Herbal extract powder | 10 |
| Carbopol 934 | 50 |
| Hydroxypropyl methyl cellulose | 25 |
| Mint extract | 5 |

The cap coating for the sticker tablets formed using the materials listed in Table A was composed of a mixture of 5 mg of Mg-stearate and 5 mg Carbopol:HPMC 2:1 w/w.

TABLE B

| Ingredient | Amount (mg) |
| --- | --- |
| Herbal extract powder | 10 |
| Benzocaine | 10 |
| Carbopol 934 | 50 |
| Hydroxypropylmethyl cellulose | 25 |
| Mint extract | 5 |

The cap coating the sticker tablets formed using the materials listed in Table B was composed of a mixture of 5 mg of Mg-stearate and 5 mg Carbopol:HPMC 2:1 w/w.

TABLE C

| Ingredient | Amount (mg) |
| --- | --- |
| Herbal extract powder | 10 |
| Lidocaine | 5 |
| Carbopol 934 | 50 |
| Hydroxypropyl methyl cellulose | 15 |
| Mint extract | 5 |

The cap coating the sticker tablets formed using the materials listed in Table C was composed of a mixture of 5 mg of Mg-stearate and 5 mg Carbopol:HPMC 2:1 w/w.

TABLE D

| Ingredient | Amount (mg) |
| --- | --- |
| Herbal powder extract | 10 |
| Amphotericine | 3 |
| Carbopol 934 | 50 |
| Hydroxypropyl methyl cellulose | 10 |
| Nane flavor | 5 |

The cap coating the sticker tablets formed using the materials listed in Table D was composed of a mixture of 5 mg of Mg-stearate and 5 mg Carbopol:HPMC 2:1 w/w.

TABLE E

| Ingredient | Amount (mg) |
| --- | --- |
| Herbal extract powder | 10 |
| Dextranase enzyme | 320,000 units |
| Carbopol 934 | 50 |
| Hydroxypropyl methyl cellulose | 25 |
| Mint extract | 5 |

The cap coating the sticker tablets formed using the materials listed in Table E composed of a mixture of 5 mg of Mg-stearate and 5 mg Carbopol:HPMC 2:1 w/w.

Administration of Bioadhesive Compositions

The above sticker tablet compositions were used by patients exhibiting herpetic stomatitis lesions (fever blisters or cold sores) and three patients with aphthous ulcers (canker sores), mucosal inflammation, toothache, recurrent aphthous stomatitis (RAS), or lesions on the lips, tongue, and gingiva. Treatment consisted of topical application of the sticker tablet once a day at the lesion site.

Treatment resulted in significant improvement within one day of placing the sticker tablets. In all cases the sticker tablets remained on the site for at least 6 hours with slow dissolution of the device.

Example 4

Clinical Study on Menthol-Loaded Sticker Tablets

Sticker tablets loaded with 2 mg menthol as the active agent were prepared by double compression, wherein the adhesive layer was composed of Carbopol™ 940 and hydroxypropyl-methyl cellulose (HPMC) at a 4:1 w/w ratio and the upper layer, which was loaded with menthol and other additives, was prepared by mixing menthol in Carbopol 940™, hydroxypropyl-methyl cellulose (HPMC), and polyvinyl ppyrrolidone (PVP) at a 1:2:4 w/w ratio. Sticker tablets of 120 mg were used for treating 20 patients with recurrent aphthous stomatitis (RAS) by applying a sticker once onto the lesion. These patients suffered from aphtous ulcers a few times during a month with one to three lesions each time.

Treatment resulted in significant improvement for all patients. The soreness and pain associated with lesion was eliminated within three hours and the lesion itself was gone within 24 hours. Eleven of the twenty patients who used the stickers for several weeks did not have a recurrence of the lesion for at least two months.

The remaining patients exhibited less frequent and less severe occurrence of the lesions. It should be noted that all patients responded well to the device with high compliance.

For comparison, single layered 120 mg sticker tablets prepared from 2:1 Carbopol 940™:HPMC loaded with 2 mg menthol were adhered to the oral mucosal tissue of 5 patients. After 60 minutes, the sticker tablets were removed due to complaints by the volunteers of etching and discomfort and the mucosal tissue was examined. A pronounced irritation and redness was found at the site of the sticker tablet which lasted for about 24 hours. Longer stays on the oral mucosal tissue intensified these symptoms. This study demonstrated the need for controlled dosing of irritating active agents, such as menthol, when administering to the mucosal tissue. Bilayer tablets in which menthol was present only in the upper layer and not in the bioadhesive layer provides a controlled release of menthol which avoids irritating effects in the oral mucosa. The adhesive layer regulates the diffusion of menthol from the upper layer in a controlled manner so that only a small amount of menthol is release onto the oral mucosa.

Example 5

Sticker Tablets Releasing Combinations of Active Agents

Sticker tablets were prepared by mixing fine powders of the active agents and the inert adhesive powders and compressing them into sticker tablets. The sticker tables were loaded with one or more local anesthetics.

The following drugs were incorporated in different combinations:
Anti-microbial: chlorhexidine, povidone-iodine, picoxidine, iodoform, triclosan
Anti-biotics: tetracycline, sulfadiazine, ofloxacin, trimethoprim
Anti-fungals: amphotericine B, nystatin, miconazole, triazoles,
Anesthetic: lidocaine, benzocaine, tetracaine, codeine, cocaine,
Antiproliperative/anticollagenase agents such as cyclosporin and rapamycin
Anti-puritic: camphor, phenol, menthol,
Anti-viral: acyclovir, acridineamine
Anti-ulceratives: acetoxolone, sucralfate, teprenone, omeprazole
Salts: sodium fluoride, Carnallite and its individual salts.

Sticker tablets with the following compositions, Compositions A, B, C, D, and E, provided in the tables below were prepared:

| Ingredient | Amount (mg) |
|---|---|
| Composition A | |
| Benzocaine | 8 |
| Amphotericine B | 3 |
| Carbopol 940 | 50 |
| Hydroxypropyl methyl cellulose | 25 |
| Composition B | |
| Benzocaine | 6 |
| Amphotericine B | 3 |
| Ibuprofen | 4 |
| Carbopol 940 | 50 |
| Hydroxypropyl methyl cellulose | 25 |
| Composition C | |
| Benzocaine | 8 |
| Chlorhexidine | 3 |
| Carbopol 940 | 50 |
| Hydroxypropyl methyl cellulose | 25 |
| Composition D | |
| Benzocaine | 8 |
| Triamcinolone | 1 |
| Carbopol 934 | 50 |
| Hydroxypropyl methyl cellulose | 25 |
| Composition E | |
| Lidocaine | 2 |
| Chlorhexidine | 3 |
| Omeprazole | 1 |
| Guanine | 0.5 |
| Carbopol 940 | 50 |
| Hydroxypropyl methyl cellulose | 25 |

Compositions A, B, C, D, and E were compressed into separate sticker tablets having a diameter of 10 mm. Sticker tablets with a diameter of 5 mm were prepared by compressing 30 mg of the mixtures, where each component in each composition was present in the same mass ratio as listed in the tables above. Preliminary studies on patients indicated an improvement of pain relief within minutes of placing the tablets described above on their oral mucosal surfaces and healing times of 24-48 hours.

Example 7

Iodine Loaded Sticker Tablets

Iodine Loading

One gram of ethyl cellulose (EC) or hydroxypropyl Cellulose (HPC) were immersed in 30 mL aqueous $I_2$—KI solution (Lugol sol, USP, 5 g Iodine, 10 g iodide, water to 100 ml), or in its diluents of the same amount of iodine content, at room temperature for 24 hours to attain equilibrium sorption. The iodinated polymers were vacuumed filtered and rinsed at least three times with 100 ml of deionized water. The polymers were dried between sheets of filter paper in a desiccator for 24 hours at ambient temperature. The amount of iodine sorption was determined from the increase in weight of the dry film before and after loading.

Manufacture of Sticker Tablet

Iodinated polymer (10 mg) and a 1:1 mixture of HPMC and PVP (40 mg) were mixed using a mortar and pestle. Double layer sticker tablets having a diameter of 10 mm, a thickness of 1 mm and a weight of 100 mg were prepared in a two stage compression procedure. In the first stage, the adhesive layer of Carbopol™ 940:HPMC 4:1 w/w ratio was pressed. The iodine layer was added on top of the adhesive layer and pressed a second time to create the double layer sticker tablets. The sticker tablets were prepared using a laboratory Carver press (Carver Machine Works, Inc., Washington, N.C.), using a pressure of 5 ton/cm² for 30 seconds. Tablets of the same size and weight, which contained the original non-iodinated cellulose, were prepared by compression molding of the polymer powder.

Alternatively, single layer sticker tablets were prepared by gently mixing iodinated doped cellulose (20 mg) and Carbopol™ 934 (60 mg) using a mortar and pestle. Tablets of 10-mm diameter, 0.9 mm thick, were pressed by a laboratory Carver press (Carver Machine Works, Inc., Washington, N.C.), using a pressure of 3 ton/cm² for 30 seconds. Control tablets of the same size and weight, which contained non-iodinated ethyl cellulose were prepared by compression molding of the polymer powder.

In Vitro Release of Iodine

FIG. 1 shows the release profiles of bioadhesive double layered sticker tablets prepared from hydroxypropyl cellulose (HPC) and ethyl cellulose (EC) in pH 7.4 phosphate buffer. When placed in a phosphate buffer having a pH of 7.4, iodine was released constantly over 10 hours.

The single layer sticker tablets described above were attached to the bottom of 20-mL vials (once tablet per vial) and 10 mL of phosphate buffer (simulating gingival fluid, pH 6.5, 8.88 g $NaH_2PO_4*H_2O$, 12.71 g $Na_2HPO_4$, diluted up to 1000 ml with deionized water) was added to each vial. The vials were incubated at 37° C. with constant shaking of 75 rpm. At each time point, the buffer was replaced with fresh buffer. In order to increase the sensitivity of the measurement, 200 µl of a starch solution (1 g/200 ml) was added to each 2 ml sample before the optical density was measured. The optical density was determined by ultraviolet spectroscopy (Ultrospec 2100 Pro; Biochrom, Cambridge, UK) at a wavelength of 610 nm. The result was the mean of three experiments.

Results

When HPC and EC were immersed in iodine-potassium iodide solution, iodine was readily absorbed into the polymer. The treated polymers developed a characteristic orange to dark brown color, depending on the iodine concentration, suggesting formation of a complex, which remained after rinsing and vacuum drying. Table 2 shows the amount of iodine absorbed by each of the polymers as a function of the iodine concentration in the loading solution, relative to its initial weight. Iodine absorption increases with iodine concentration. At the highest concentration, HPC and EC particles exhibited an increase in mass of 91% and 46.3% respectively.

TABLE 2

The Effect of Iodine Dopant Solution on the Mass Increase of HPC and EC

| Polymer Sample No. | Polymer | Iodine Loading Solution (%) | Mass Increase (%) |
|---|---|---|---|
| 1 | HPC | 0.02 | 91 |
| 2 | EC | 0.02 | 46.3 |
| 3 | EC | 0.01 | 28.7 |
| 4 | EC | 0.005 | 9.5 |
| 5 | EC | 0.001 | 0.2 |

A series of UV-VIS absorption spectra of the $I_2$-EC complex formed by EC particles immersed in $I_2$—KI solutions at different iodine concentrations shows that EC exhibits no bands in the visible region, and the spectrum of iodine-doped ethyl cellulose shows bands that are attributable to a charge transfer complex. The absorption maxima at around 210 and 360 nm increase with increasing iodine concentration. As the UV bands arise from the complex with $I_2$—$I_3^{-5}$, the broad absorption band in the visible range is due to un-reacted $I_2$.

DSC scans of pure EC exhibit three phase transitions due to its ability to form a thermotropic liquid crystal. According to Chen et al., the transition at 188° C. is a solid-mesophase transition, and that at 228° C. is the mesophase-isotropic liquid transition (Chen et al., *J. Appl Poly. Sci.*, 45: 2153-2158 (1992)). The other transition at 135° C. is the glass transition. After iodine loading, it was found that the endotherm at 228° C. became hard to detect, while a sharp endotherm appears at 183° C. This could be the result of EC becoming more crystalline due to the complex formation and chain ordering, and to iodine sublimation, since the iodine sublimation temperature is 180° C.

Antifungal and Antibacterial In Vitro Bioassay

The antifungal and antibacterial properties of the single layer sticker tablets described above were measured. The inhibition zones around the sticker tablets, when tested with two microorganisms, *Candida albicans* and *P. gingivalis* on solid media are shown in Table 3. Each number represents one positive sample. Dose dependence inhibition of *Candida albicans* and *P. gingivalis* growth were demonstrated and the HPC-Iodine tablets caused the maximum inhibition followed by EC doped in 0.02% Iodine solution.

TABLE 3

Inhibition Zones around the Sticker Tablets

| Polymer/Iodine Dopant Solution | Diameter of Inhibition Zones Showing Complete Inhibition of Growth (mm) | |
|---|---|---|
| | *Candida albicans* | *P. gingivalis* |
| HPC/0.02% | 36 | 33 |
| EC/0.02% | 30 | 26 |
| EC/0.01% | 24 | 22.5 |
| EC/0.005% | 17 | 20 |
| EC/0.001% | 0 | 19.5 |
| Blank Tablet | 0 | 0 |

Figure 2:
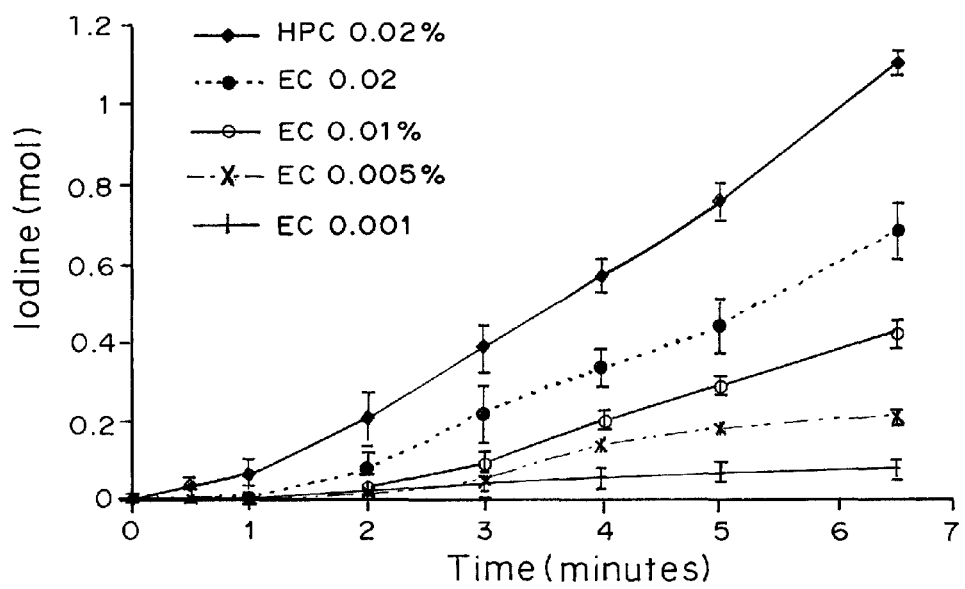
FIG. 2 shows the release profile of iodine (mol) versus time (minutes) in a pH 6.5 phosphate buffer at 37° C. from bioadhesive single layer tables prepared from hydroxypropyl cellulose (HPC) and ethyl cellulose (EC). Iodine concentration was determined by ultraviolet spectroscopy at a wavelength of 610 nm.

The different sticker tablets exhibited marked antifungal and antibacterial activity against the tested bacterial/fungal strains. This indicates that the cellulose-iodine complex, when incorporated into adhesive polymers and placed in an aqueous environment, release the iodine contents in an adequate manner as demonstrated in FIG. 2. The sticker tablets show broad spectrum antimicrobial activity.

In Vivo Experiment

Adhesive tablets loaded with iodine complexed to EC or HPC were prepared as described above. The tablets contained 5 mg iodine per 100 mg tablet. Monolayer tablets were placed onto the cheek mucosal of three volunteers and removed after 60 minutes. The effect on the tissue was observed. Local irritation, in the form of redness and swelling, was observed. The irritation subsided after 24 hours. The volunteers all reported discomfort during the period of tablet adhesion. The same group of volunteers was treated with a double layer tablet, wherein the adhesive layer did not contain iodine. No irritation or discomfort was reported, even after 4 hours of tablet adhesion. Removal of the tablet at 60 minutes and 120 minutes revealed a light yellow color on the mucosal tissue, which indicated a steady and slow diffusion of iodine to the mucosal tissue.

Further, the sticker tablets adhered very well onto oral mucosal tissue and gradually dissolved over 5 hours while releasing minute amounts of iodine which did not affect the feeling or taste.

Unless defined otherwise, all technical and scientific terms used herein have the same meanings as commonly understood by one of skill in the art to which the disclosed invention belongs. Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A solid, self-bioadhesive multilayer compression molded sticker tablet for topical application in the mouth of a human consisting essentially of:
    (a) a delivery layer consisting essentially of a component selected from the group consisting of wintergreen oil, peppermint oil, spearmint oil, clove bud oil, menthol, anethole, methyl salicylate, eucalyptol extract, cassia extract, 1-menthyl acetate, sage extract, eugenol, parsley oil, oxanone, alpha-irisone, marjoram extract, orange extract, propenyl guaethol, cinnamon extract, vanillin, thymol, linalool, cinnamaldehyde glycerol acetal, lemon oil, geraniol oil, peppermint oil, turpentine oil, peppermint oil, and mixtures thereof incorporated into or encapsulated into a water-swellable material such that it is releasable from the water-swellable material once placed in the mouth of the human;
    wherein the water-swellable material is selected from the group consisting of hydroxypropyl cellulose, hydroxypropyl methylcellulose, hydroxyethylcellulose, carboxymethyl cellulose, dextran, arabinogalactan, pullulan, guar gum, hyaluronic acid, pectin, and mixtures thereof; and
    wherein the water-swellable material has sufficient hydrophobicity to maintain integrity of the tablet during release of the component and
    (b) a non-irritating bioadhesive layer consisting essentially of a bioadhesive polyacrylic acid;
    wherein upon application to a mucosal surface of the mouth of the human, the tablet adheres to mucosal surface tissue of the mouth of the human for between about 3 and 10 hours, and
    wherein upon adhesion to the mucosal surface of the human, the delivery layer releases a non-irritating therapeutically effective dose of the component to treat mucosal disease in the mouth of a human for a period of at least three hours.

2. The sticker tablet of claim 1, wherein the component is peppermint oil.

3. The sticker tablet of claim 1, wherein the component is menthol.

* * * * *